United States Patent [19]

Kraatz et al.

[11] Patent Number: 4,988,734
[45] Date of Patent: Jan. 29, 1991

[54] FUNGICIDAL STEREOISOMERS OF N-(R)-(1-ARYL-ETHYL)-1-ALKYL-2,2,-DICHLORO-CYCLOPROPANECARBOXAMIDES

[75] Inventors: Udo Kraatz; Gerd Hänssler, both of Leverkusen, Fed. Rep. of Germany

[73] Assignee: Bayer Aktiengesellschaft, Leverkusen, Fed. Rep. of Germany

[21] Appl. No.: 337,494

[22] Filed: Apr. 13, 1989

[30] Foreign Application Priority Data

May 7, 1988 [DE] Fed. Rep. of Germany ....... 3815728

[51] Int. Cl.$^5$ .................. A61K 31/165; C07C 233/59
[52] U.S. Cl. ..................................... 514/624; 564/190
[58] Field of Search ......................... 514/624; 564/190

[56] References Cited

U.S. PATENT DOCUMENTS 4,710,518 12/1987 Kurahashi et al. ................. 514/624

FOREIGN PATENT DOCUMENTS

| 0170842 | 2/1986 | European Pat. Off. . |
| 0257448 | 3/1988 | European Pat. Off. . |
| 0257448 | 3/1988 | European Pat. Off. . |
| 63-27407 | 2/1988 | Japan . |
| 63-54349 | 3/1988 | Japan . |

Primary Examiner—Richard L. Raymond
Assistant Examiner—Peter G. O'Sullivan
Attorney, Agent, or Firm—Sprung Horn Kramer & Woods

[57] ABSTRACT

Highly fungicidal stereoisomers of N-(R)-(1-aryl-ethyl)-1-alkyl-2,2-dichloro-cyclopropanecarboxamides of the formula

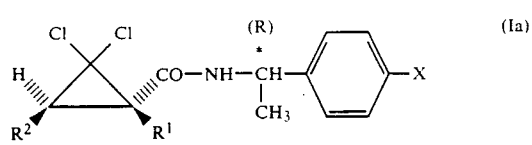

or

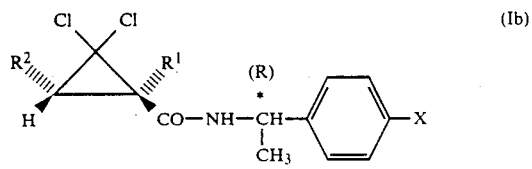

or a mixture thereof, substantially free of other stereoisomers, in which
  $R^1$ stands for optionally branched alkyl having 2 to 4 carbon atoms,
  $R^2$ stands for hydrogen, methyl or ethyl and X stands for hydrogen or halogen.

Also new are intermediates of the formula

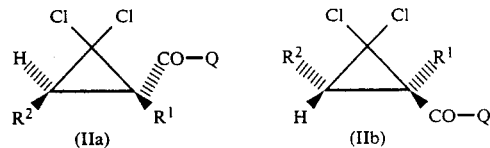

or mixtures thereof, substantially free of other stereoisomers, in which
  $R^1$ stands for optionally branched alkyl having 2 to 4 carbon atoms.
  $R^2$ stands for hydrogen, methyl or ethyl, and Q stands for Cl, OH, or methoxy or ethoxy.

6 Claims, No Drawings

FUNGICIDAL STEREOISOMERS OF N-(R)-(1-ARYL-ETHYL)-1-ALKYL-2,2,-DICHLORO-CYCLOPROPANECARBOXAMIDES

The present invention relates to new stereoisomers of N-(R)-(1-aryl-ethyl)-1-alkyl-2,2-dichloro-cyclopropanecarboxamides, a process for their preparation and their use for combating pests, in particular fungi.

It has already been disclosed that isomer mixtures of certain cyclopropanecarboxamides, such as, for example, of N-(1-(4-chloro-phenyl)-ethyl)-2,2-dichloro-1-ethyl-3-methylcyclopropanecarboxamide, exhibit fungicidal properties (cf. EP-A 170,842/U.S. Pat. No. 4,710,518). However, the action of the known compounds is not satisfactory in all respects.

Certain optically active forms of substituted cyclopropanecarboxamides have also already been disclosed (cf. EP-A 257,448).

New stereoisomers of N-(R)-(1-aryl-ethyl)-1-alkyl-2,2-dichloro-cyclopropanecarboxamides of the formulae (Ia) and (Ib)

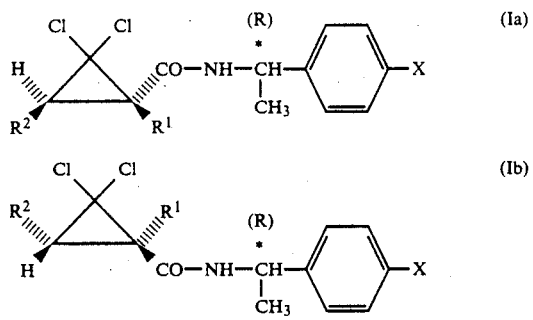

in which $R^1$ stands for optionally branched alkyl having 2 to 4 carbon atoms, $R^2$ stands for hydrogen, methyl or ethyl and X stands for hydrogen or halogen, have now been found.

The invention relates both to the individual stereoisomers of the formulae (Ia) and (Ib) and to their mixtures.

The new compounds of the formulae (Ia) and (Ib) are obtained when—for the preparation of their mixtures in a first step—mixtures of (1R)- and (1S)-1-alkyl-2,2-dichloro-cyclopropanecarbonyl chlorides of the formulae (IIa) and (IIb)

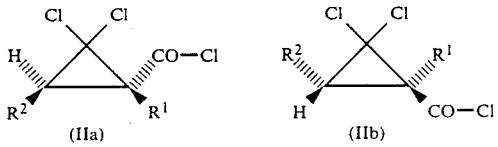

in which $R^1$ and $R^2$ have the abovementioned meanings, are reacted with (R)-1-aryl-ethylamines of the formula (III)

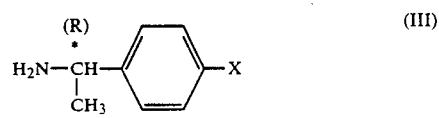

in which

X has the abovementioned meaning, if appropriate in the presence of an acid acceptor and if appropriate in the presence of a diluent, and when, if appropriate, for the preparation of the individual stereoisomers of the formulae (Ia) and (Ib)—the resulting mixtures of the diastereomers of the compounds of the formulae (Ia) and (Ib) are separated in a second step by customary methods on the basis of the different physical properties.

The new stereoisomers of N-(R)-(1-aryl-ethyl)-1-alkyl-2,2-dichloro-cyclopropanecarboxamides of the formulae (Ia) and (Ib) and their mixtures are distinguished by a powerful action against pests, mainly against fungi.

Surprisingly, the new stereoisomers of the formulae (Ia) and (Ib), in particular those of the formula (Ia) and also the mixtures of the compounds of the formulae (Ia) and (Ib) show, inter alia, a considerably more powerful fungicidal action than the known mixture of the isomers of N-(1-(4-chloro-phenyl)-ethyl)-2,2-dichloro-1-ethyl-3-methyl-cyclopropanecarboxamide.

The invention preferably relates to the stereoisomers of the formula (Ia) and to mixtures of the stereoisomers of the formulae (Ia) and (Ib) which contain at least 50% of the stereoisomers of the formula (Ia), where $R^1$ stands for ethyl, propyl or isopropyl, $R^2$ stands for hydrogen or methyl and X stands for hydrogen, fluorine, chlorine or bromine.

If a 1:1 mixture of (1R)- and (1 S)-2,2-dichloro-1-ethyl-3t-methyl-1r-cyclopropanecarbonyl chloride (nomenclature cf. Beilstein) and (R)-1-phenyl-ethylamine are used as starting substances, the course of the reaction in the first step of the process according to the invention can be represented by the following equation:

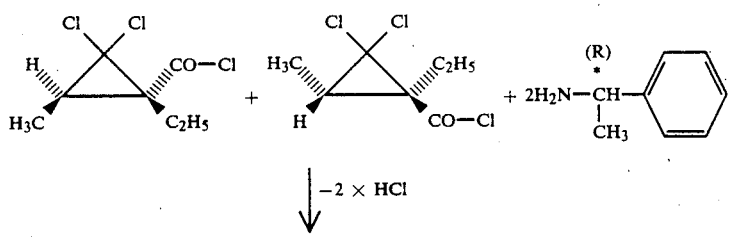

$\downarrow -2 \times HCl$

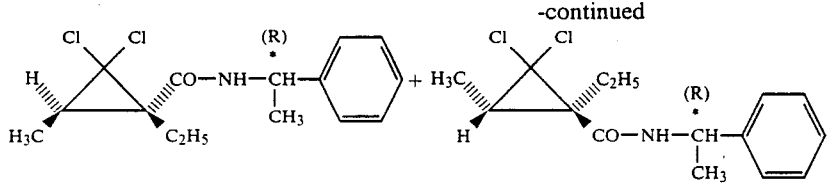

Formulae (IIa) and (IIb) provide general definitions of the 1-alkyl-2,2-dichloro-cyclopropanecarbonyl chlorides to be used as starting substances in the process according to the invention for the preparation of compounds of the formula (Ia) and (Ib). In formulae (IIa) and (IIb), $R^1$ and $R^2$ preferably have those meanings which have already been preferably mentioned above for $R^1$ and $R^2$ in connection with the description of the compounds of the formulae (Ia) and (Ib) according to the invention.

Examples of the starting substances of the formulae (IIa) and (IIb) which may be mentioned are: (1R)- and (1S)-2,2-dichloro-1-ethyl-3t-methyl-1r-cyclopropanecarbonyl chloride, (1R)- and (1S)-2,2-dichloro-3t-methyl-1-propyl-1r-cyclopropanecarbonyl chloride, (1R)- and (1S)-2,2-dichloro-1-isopropyl-3t-methyl-1r-cyclopropanecarbonyl chloride, (1R)- and (1S)-2,2-dichloro-1-ethylcyclopropanecarbonyl chloride, (1R)- and (1S)-2,2-dichloro-1-propyl-cyclopropanecarbonyl chloride and also (1R)- and (1S)-2,2-dichloro-1-isopropyl-cyclopropanecarbonyl chloride.

The starting substances of the formulae (IIa) and (IIb) were hitherto unknown from the literature. 1:1 mixtures of compounds of the formulae (IIa) and (IIb) are obtained when corresponding mixtures of (1R)- and (1S)-1-alkyl-2,2-dichlorocyclopropanecarboxylic acids of the formulae (IIIa) and (IIIb)

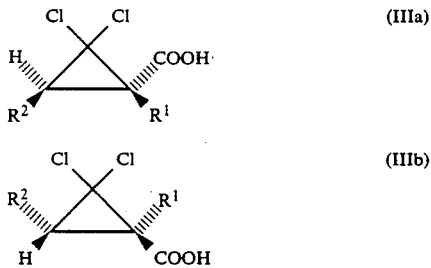

in which $R^1$ and $R^2$ have the abovementioned meanings, are reacted with a chlorinating agent, such as, for example, thionyl chloride, if appropriate in the presence of a catalyst, such as, for example, dimethylformamide, and if appropriate in the presence of a diluent, such as, for example, methylene chloride, at temperatures between 10° C. and 50° C.

Formulae (IIIa) and (IIIb) provide general definitions of the 1-alkyl-2,2-dichlorocyclopropanecarboxylic acids required as starting substances. In formulae (IIIa) and (IIIb), $R^1$ and $R^2$ preferably have those meanings which have already been preferably mentioned above for $R^1$ and $R^2$ in connection with the description of the compounds of the formula (Ia) and (Ib) according to the invention.

Examples of the starting substances of the formulae (IIIa) and (IIIb) which may be mentioned are: (1R)- and (1S)-2,2-dichloro-1-ethyl-3t-methyl-1R-cyclopropanecarboxylic acid, (1R)- and (1S)-2,2-dichloro-3t-methyl-1-propyl-1r-cyclopropanecarboxylic acid, (1R)- and (1S)-2,2-dichloro-1-isopropyl-3 t-methyl-1r-cyclopropanecarboxylic acid, (1R)- and (1S)-2,2-dichloro-1-ethyl-cyclopropanecarboxylic acid, (1R)- and (1S)-2,2-dichloro-1-propyl-cyclopropanecarboxylic acid and also (1R)- and (1S)-2,2-dichloro-1-isopropyl-cyclopropanecarboxylic acid.

The starting substances of the formula (IIIa) and (IIIb) were hitherto unknown from the literature. 1:1 mixtures of compounds of the formulae (IIIa) and (IIIb) are obtained when corresponding mixtures of (1R)- and (1S)-1-alkyl-2,2-dichloro-cyclopropanecarboxylates of the formulae (IVa) and (IVb)

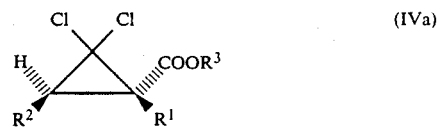 (IVa)

 (IVb)

in which $R^1$ and $R^2$ have the abovementioned meanings and $R^3$ stands for alkyl, preferably for methyl or ethyl, are reacted with an aqueous alkali metal hydroxide solution, such as, for example, sodium hydroxide solution, if appropriate in the presence of an organic solvent, such as, for example, methanol or ethanol, at temperatures between 20° C. and 100° C. and the mixture is then acidified using a strong acid, such as, for example, hydrochloric acid.

Formulae (IVa) and (IVb) provide general definitions of the 1-alkyl-2,2-dichloro-cyclopropanecarboxylates required as starting substances. In formulae (IVa) and (IVb), $R^1$ and $R^2$ preferably have those meanings which have already been preferably mentioned above for $R^1$ and $R^2$ in connection with the description of the compounds of the formulae (Ia) and (Ib) according to the invention, and $R^3$ preferably stands for methyl or ethyl.

Examples of the starting substances of the formulae (IVa) and (IVb) which may be mentioned are: methyl (1R)- and (1S)-2,2-dichloro-1-ethyl-3t-methyl-1r-cyclopropanecarboxylate and ethyl (1R)- and (1S)-2,2-dichloro-1-ethyl-3t-methyl-1r-cyclopropanecarboxylate, methyl (1R)- and (1S)-2,2-dichloro-1-isopropyl-3 t-methyl-1r-cyclopropanecarboxylate and ethyl (1R)- and (1S)-2,2-dichloro-1-isopropyl-3-t-methyl-1r-cyclopropanecarboxylate, methyl (1R)- and (1S)-2,2-dichloro-1-ethyl-cyclopropanecarboxylate and ethyl (1R)- and (1S)-2,2-dichloro-1-ethyl-cyclopropanecarboxylate, methyl (1R)- and (1S)-2,2-dichloro-1-propyl-cyclopropanecarboxylate and ethyl (1R)- and (1S)-2,2-dichloro-1-propyl-cyclopropanecarboxylate and also methyl (1R)- and (1S)-2,2-dichloro-1-isopropyl-cyclopropanecarboxylate and ethyl (1R)- and (1S)-2,2-dichloro-1-isopropyl-cyclopropanecarboxylate.

The starting substances of the formulae (IVa) and (IVb) were hitherto unknown from the literature. 1:1 mixtures of compounds of the formulae (IVa) and (IVb) are obtained when alkenecarboxylates of the formula (V)

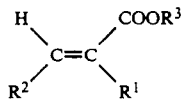

in which $R^1$, $R^2$ and $R^3$ have the abovementioned meanings, are reacted—if appropriate in the presence of diluents, such as, for example, chloroform and water, and if appropriate in the presence of a phase transfer catalyst, such as, for example, tetrabutylammonium bromide, at temperatures between 10° C. and 60° C.—with dichlorocarbene, which is, if appropriate, prepared in situ, for example from chloroform and a strong base, such as, for example, sodium hydroxide or potassium hydroxide.

The starting substances of the formula (V) are already known (cf. J. Organomet. Chem. 96 (1975), 163–168).

Formula (III) provides a general definition of the (R)-1-aryl-ethylamines also to be used as starting substances in the process according to the invention for the preparation of compounds of the formulae (Ia) and (Ib).

In formula (III), X preferably has the meaning which has already been preferably mentioned above for X in connection with the description of the compounds of the formulae (Ia) and (Ib) according to the invention.

Examples of the starting substances of the formula (III) which may be mentioned are:

(R)-1-Phenyl-ethylamine, (R)-1-(4-fluoro-phenyl)-ethylamine, (R)-1-(4-chloro-phenyl)-ethylamine and (R)-1-(4-bromo-phenyl)-ethylamine.

The starting substances of the formula (III) are already known (cf. Indian J. Chem. 13 (1975), 631).

The first step of the process according to the invention for the preparation of the new stereoisomers of the formula (I) is preferably carried out using diluents. Suitable diluents for this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the first step of the process according to the invention are all acid-binding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In the first step of the process according to the invention, the reaction temperatures can be varied within a relatively wide range. In general, the first step of the process is carried out at temperatures between −20° C. and +80° C., preferably at temperatures between 0° C. and 50° C.

In the first step, the process according to the invention is generally carried out under atmospheric pressure.

For carrying out the first step of the process according to the invention, the starting substances required in each case are generally employed in approximately equimolar amounts. However, it is also possible to use one of the two components employed in each case in relatively large excess. The reactions are generally carried out in a suitable diluent in the presence of an acid acceptor, and the reaction mixture is stirred for several hours at the specific temperature required. Working-up after the first step of the process according to the invention is carried out by customary methods.

In general, a procedure is followed in which the reaction mixture—if appropriate after concentration—is shaken with water and a virtually water-immiscible organic solvent, such as, for example, methylene chloride, the organic phase is washed with an aqueous mineral acid, such as, for example, hydrochloric acid, dried and filtered, the filtrate is evaporated, the residue is crystallized by trituration with a suitable solvent, such as, for example, cyclohexane, and the crystals are filtered off with suction.

In the second step, the diastereomers (Ia) and (Ib) can be separated using methods which are suitable for such purposes, that is, for example, fractional crystallization or alternatively with the aid of chromatographic methods.

Column-chromatographic separation methods are particularly preferably employed, such as, for example, high-pressure filtration over a silica gel column using an elution mixture of hexane, cyclohexane, methyl tert-butyl ether, heptane, carbon tetrachloride and/or propionitrile.

The active compounds according to the invention exhibit a powerful biological action and can be employed in practice for combating undesired pests. The active compounds are suitable for use as plant protection agents, mainly as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* on rice.

Depending on their specific physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable, for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable, for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable, for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable, for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

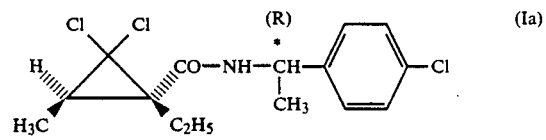

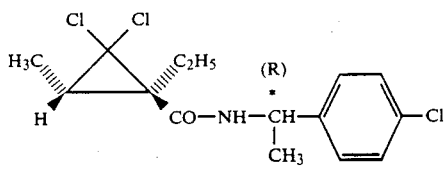 (Ib)

9.5 g (44 mmol) of a 1:1 mixture of (1R)- and (1S)-2,2-dichloro-1-ethyl-3t-methyl-1r-cyclopropanecarbonyl chloride are added to a stirred mixture of 6.2 g (40 mmol) of (R)-1-(4-chloro-phenyl)-ethylamine, 4.8 g (48 mmol) of triethylamine and 40 ml of the methylene chloride, with ice cooling. The reaction mixture is then stirred for 4 hours at 20° C., diluted with water and methylene chloride and shaken. The organic phase is separated off, washed with 2N hydrochloric acid, dried using magnesium sulphate and filtered. The solvent is distilled off from the filtrate under a waterpump vacuum, and the product which remains in the residue is crystallized by trituration with cyclohexane and isolated by filtering off with suction.

13.8 g (98% of theory) of a mixture of diastereomers (1a/1b) of N-(R)-(1-(4-chloro-phenyl)-ethyl)-2,2-dichloro-1-ethyl-3t-methyl-1r-cyclopropanecarboxamide of melting point 144° C.–146° C. are obtained. $[\alpha]_D^{25}$: +40.92 (CHCl$_3$, c=5.1).

10 g (30 mmol) of the mixture of diastereomers are separated using HPLC (high performance liquid chromatography) on a silica gel column (Merck, 5–20μ grain size) using the eluent mixture heptane/methyl tert-butyl ether (85:15).

4.1 g of N-(R)-(1-(4-chloro-phenyl)-ethyl)-(1R)-2,2-dichloro-1-ethyl-3t-methyl-1r-cyclopropanecarboxamide (1b) of melting point 158° C. are eluted as the first fraction. $[\alpha]_D^{25}$: +20.05 (CHCl$_3$, c=2.00).

4.4 g of N-(R)-(1-(4-chloro-phenyl)-ethyl)-(1S)-2,2-dichloro-1-ethyl-3t-methyl-1r-cyclopropanecarboxamide (1a) of melting point 154° C. are obtained as the second fraction. $[\alpha]_D^{25}$: +61.01 (CHCl$_3$, c=2.03).

The compounds listed below can be obtained in analogy to Example 1.

EXAMPLE 2

Example 2

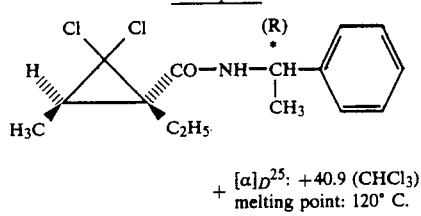

+ $[\alpha]_D^{25}$: +40.9 (CHCl$_3$)
melting point: 120° C.

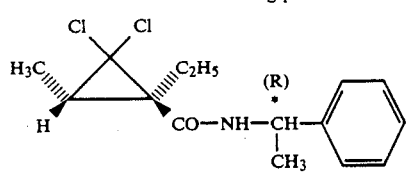

Example 3

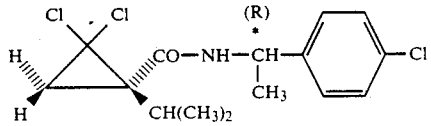

+

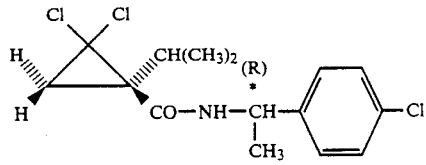

Starting Substances of the Formulae (IIa) and (IIb)

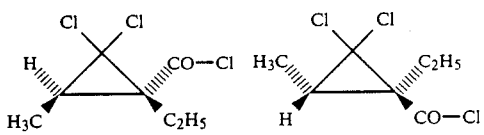

29 g (0.15 mol) of a 1:1 mixture of (1R)- and (1S)-2,2-dichloro-1-ethyl-3t-methyl-1r-cyclopropanecarboxylic acid (IIIa/IIIb) are dissolved in 30 ml of methylene chloride. 2 drops of dimethylformamide are then added and subsequently 28.6 g (0.24 mol) of thionyl chloride are added dropwise to the stirred mixture, and the mixture is refluxed for a further 30 minutes. Working up is then carried out by distillation under a waterpump vacuum.

25 g (78% of theory) of a 1:1 mixture of (1R)- and (1S)-2,2-dichloro-1-ethyl-3t-methyl-1r-cyclopropanecarbonyl chloride of boiling point 80° C.–85° C. are obtained (15 Torr/2 kPa).

Starting Substances of the Formulae (IIIa) and (IIIb)

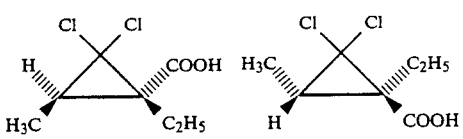

A solution of 67 g (1.675 mol) of sodium hydroxide in 80 ml of water is added to a solution of 185 g (0.82 mol) of a 1:1 mixture of ethyl (1R)- and (1S)-2,2-dichloro-1-ethyl-3t-methyl-1r-cyclopropanecarboxylate in 400 ml of ethanol and the reaction mixture is stirred at 80° C. for 3 hours. Most of the ethanol is then distilled off under a waterpump vacuum, and the residue is diluted with water and acidified with 10% strength hydrochloric acid. The mixture is then extracted using methylene chloride, the organic phase is concentrated, the residue is crystallized by trituration with petroleum ether and the product is isolated by filtering off with suction.

108 g (67% of theory) of a 1:1 mixture of (1R)- and (1S)-2,2-dichloro-1-ethyl-3t-methyl-1r-cyclopropanecarboxylic acid of melting point 77° C.–79° C. are obtained.

Starting Substances of the Formulae (IVa) and (IVb)

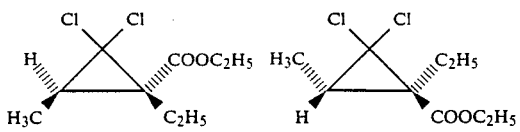

A solution of 405 g (6.4 mol) of 88% strength potassium hydroxide solution in 307 ml of water and also 8.3 g (0.026 mol) of tetrabutylammonium bromide are added to a solution of 181 g (1.28 mol) of ethyl E-2-ethyl-2-butenoate in 550 ml of chloroform and the reaction mixture is stirred vigorously at 40° C. for 20 hours. The organic phase is then separated off, washed with 1N hydrochloric acid and distilled under a waterpump vacuum.

185 g (64% of theory) of a 1:1 mixture of ethyl (1R)- and (1S)-2,2-dichloro-1-ethyl-3t-methyl-1r-cyclopropanecarboxylate of boiling point 95° C.-102° C. (15 Torr/2 kPa) are obtained.
*Nomenclature (E/Z) cf. J. Am. Chem. Soc. 90 (1968), 509-510.

Starting Substances of the Formula (II)

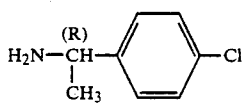

The solutions, which have been heated to approximately 60° C.-70° C., of 91.9 (0.587 mol) of racemic p-chlorophenethylamine in 300 ml of ethanol and 122 g of (s)-(−)-O-(N-phenylcarbamoyl) lactic acid in 800 ml of ethanol are combined and left to stand overnight. The crystalline slurry is filtered off with suction (93 g) and is treated with 200 ml of 10% strength sodium hydroxide solution/300 ml of methylene chloride. The organic phase is washed with water, dried over magnesium sulphate and evaporated on a rotary evaporator.

44.5 g of the (+)-enantiomer of optical purity 89.4% e.e. (enantiomeric excess) are obtained.

44 g (0.28 mol) of this amine are dissolved in 150 ml of ethanol, heated to 60° C. and combined with a solution, likewise warmed to 60° C., of 59 g (0.28 mol) of (S)-(−)-O-(N-phenylcarbamoyl)lactic acid in 400 ml of ethanol. The salt, which crystallizes out slowly, is filtered off with suction following standing overnight (74 g) and cleaved as described above using 300 ml of methylene chloride/10% strength sodium hydroxide solution.

After washing, drying and concentrating the organic phase, 40.4 g (88.8% of theory) of the (+)-enantiomer of optical purity 97.4% e.e. (enantiomeric excess) are obtained.

USE EXAMPLE

Pyricularia test (rice)/protective Solvent: 12.5 parts by weight of acetone Emulsifier: 0.3 part by weight of alkylaryl polyglycol ether.

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the compound of the formula (1a) according to the invention shows a clearly superior activity compared with the prior art.

TABLE

| Active compound | Pyricularia test (rice)/protective | |
|---|---|---|
| | Concentration of active compound in % | Degree of effectiveness as % of the untreated control |
| ![structure] (known) | 0.0025 | 30 |
| ![structure] (1a) | 0.0025 | 89 |

It will be appreciated that the instant specification and claims are set forth by way of illustration and not limitation, and that various modifications and changes may be made without departing from the spirit and scope of the present invention.

What is claimed is:

1. The stereoisomer N-(R)-(1-(4-chloro-phenyl)ethyl)-(1S)-2,2-dichloro-1-ethyl-3t-methyl-1-cyclopropanecarboxamide of the formula

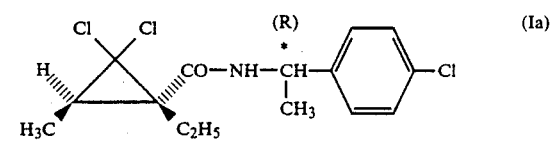

substantially free of other stereoisomers.

2. A mixture consisting of the stereoisomer N-(R)-(1-(4-chloro-phenyl)-ethyl-(1S)-2,2-dichloro-1-ethyl-3t-methyl-1-cyclopropanecarboxamide of the formula

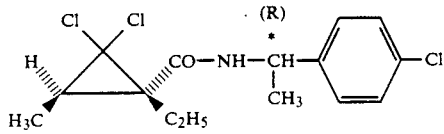

and the stereoisomer N-(R)-(1-(4-chloro-phenyl)-ethyl)-(1R)-2,2-dichloro-1-ethyl-3t-methyl-1-cyclopropanecarboxyamide, substantially free of other isomers.

3. A fungicidal composition comprising a fungicidally effective amount of the stereoisomer according to claim 1 and a diluent.

4. A fungicidal composition comprising a fungicidally effective amount of the stereoisomer mixture according to claim 2 and a diluent.

5. A method of combating fungi which comprises applying to such fungi a fungicidally effective amount of the stereoisomer according to claim 1.

6. A method of combating fungi which comprises applying to such fungi a fungicidally effective amount of the stereoisomer mixture according to claim 2.

* * * * *